(12) United States Patent
Mosbey et al.

(10) Patent No.: US 8,026,327 B2
(45) Date of Patent: Sep. 27, 2011

(54) WATER-IN-OIL EMULSIONS WITH ETHYLENE OXIDE GROUPS, COMPOSITIONS, AND METHODS

(75) Inventors: Deral T. Mosbey, Lake Elmo, MN (US); Gilbert L. Eian, Mahtomedi, MN (US); Matthew T. Scholz, Woodbury, MN (US); Richard A. Mallo, Woodbury, MN (US); Ling Lu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1300 days.

(21) Appl. No.: 11/256,135

(22) Filed: Oct. 21, 2005

(65) Prior Publication Data

US 2006/0034798 A1 Feb. 16, 2006

Related U.S. Application Data

(62) Division of application No. 09/966,511, filed on Sep. 28, 2001, now Pat. No. 7,030,203.

(51) Int. Cl.
  *C08F 20/10* (2006.01)
  *A61K 6/00* (2006.01)
(52) U.S. Cl. .................. 526/318.44; 526/318; 424/401; 424/404; 424/70.1; 514/844; 514/845
(58) Field of Classification Search .................. 424/401, 424/405, 404, 70.1; 526/318.44, 318; 514/844, 514/845
  See application file for complete search history.

(56) References Cited

U.S. PATENT DOCUMENTS

| | | | |
|---|---|---|---|
| 3,917,822 A | 11/1975 | Turney | |
| 4,147,681 A | 4/1979 | Lim et al. | 260/29.6 |
| 4,172,122 A | 10/1979 | Kubik et al. | |
| 4,552,685 A | 11/1985 | Kernstock et al. | 252/355 |
| 4,552,755 A | 11/1985 | Randen | |
| 4,816,256 A | 3/1989 | Randen | |
| 4,847,078 A | 7/1989 | Sheppard et al. | 424/80 |
| 4,940,579 A | 7/1990 | Randen | |
| 5,075,400 A | 12/1991 | Andrade et al. | |
| 5,296,573 A | 3/1994 | Esselborn et al. | |
| 5,318,995 A | 6/1994 | Mondet et al. | 514/772 |
| 5,389,676 A * | 2/1995 | Michaels | 514/556 |
| 5,531,993 A | 7/1996 | Griat | |
| 5,712,359 A | 1/1998 | Auschra et al. | 526/329 |
| 5,733,570 A | 3/1998 | Chen et al. | |
| 5,853,750 A | 12/1998 | Dietz et al. | 424/448 |
| 5,935,589 A | 8/1999 | Mukherjee et al. | 424/401 |
| 5,951,993 A | 9/1999 | Scholz et al. | |
| 6,086,911 A | 7/2000 | Godbey | |
| 6,200,596 B1 | 3/2001 | Schwartzmiller et al. | |
| 6,228,354 B1 | 5/2001 | Jeng | 424/78.07 |
| 6,495,158 B1 | 12/2002 | Buseman et al. | |
| 6,562,354 B1 | 5/2003 | Afriat et al. | 424/401 |
| 6,645,476 B1 | 11/2003 | Morschhauser et al. | 424/70.1 |
| 6,838,078 B2 | 1/2005 | Wang et al. | 424/78.02 |
| 6,951,642 B2 | 10/2005 | Scholz et al. | 424/78.17 |
| 7,030,203 B2 | 4/2006 | Mosbey et al. | |
| 2001/0029247 A1 | 10/2001 | Boures et al. | |
| 2003/0031643 A1 | 2/2003 | L'alloret et al. | 424/70 |
| 2003/0064046 A1 | 4/2003 | Omura et al. | 424/70.12 |
| 2003/0175503 A1 | 9/2003 | Lucast et al. | 428/343 |
| 2006/0029569 A1 | 2/2006 | Scholz et al. | |

FOREIGN PATENT DOCUMENTS

| | | |
|---|---|---|
| EP | 0 011 806 | 6/1980 |
| EP | 0 011 806 | 11/1983 |
| EP | 0 446 636 A2 | 9/1991 |
| EP | 0 522 756 A1 | 1/1993 |
| EP | 0 661 964 B1 | 7/1995 |
| EP | 0 480 189 B1 | 3/1996 |
| EP | 0 761 095 A2 | 3/1997 |
| EP | 0 913 445 A1 | 5/1999 |
| EP | 1 069 142 A1 | 1/2001 |
| JP | 8-048727 | 2/1996 |
| JP | 10-139625 | 5/1998 |
| JP | 11-029459 | 2/1999 |
| JP | 2001-059054 | 3/2001 |
| JP | 2003-012444 | 1/2003 |
| WO | WO 96/03164 A1 | 2/1996 |
| WO | WO 97/45101 | 12/1997 |
| WO | WO 01/01949 | 1/2001 |
| WO | WO 02/43689 A2 | 6/2002 |

OTHER PUBLICATIONS

Billmeyer, Jr., *Textbook of Polymer Science, Second Edition*, Wiley-Interscience, New York, NY; title page, publication page, and pp. 84-85 (1971).

Cárdenas-Valera et al., "Graft copolymers as stabilizers for oil-in-water emulsions Part 1. Synthesis of the copolymers and their behaviour as monolayers spread at the air-water and oil-water interfaces," *Colloids and Surfaces A: Physicochemical and Engineering Aspects*, 96:53-67 (1995).

Cárdenas-Valera et al., "Graft copolymers as stabilizers for oil-in-water emulsions Part 2. Preparation of the emulsions and the factors affecting their stability," *Colloids and Surfaces A: Physicochemical and Engineering Aspects*, 97:1-12 (1995).

ICI Companies Datasheet, "ICI Surfactants Arlacel® P135 Polymeric Emulsifier," 1 page (undated).

ICI Companies Product Brochure, "Arlacel® P135 Polymeric Emulsifier," Wilmington, DE; 7 pages (Aug. 1997).

Satas, ed., *Handbook of Pressure Sensitive Adhesive Technology 2nd Edition*, Van Nostrand Reinhold, New York, NY; title page, publication page, and p. 172 (1989).

(Continued)

*Primary Examiner* — Gina C Yu
(74) *Attorney, Agent, or Firm* — Thomas M. Spielbauer

(57) ABSTRACT

Water-in-oil emulsions, compositions, and methods that include a vinyl polymer that includes ethylene oxide-containing side chains and alkyl-Y-containing side chains, wherein Y is O or NR, wherein R is H or $CH_3$, and wherein the alkyl group of the alkyl-Y-containing side chain has at least 4 carbon atoms on average in a cyclic, branched-, or straight-chain configuration and optionally including one or more heteroatoms.

23 Claims, No Drawings

OTHER PUBLICATIONS

Weast, ed., *CRC Handbook of Chemistry and Physics, 56th Edition*, CRC Press, Cleveland, OH; title page, publication page, preface, and p. D-150 (1975).

Wenninger et al., eds., *The International Cosmetic Ingredient Dictionary and Handbook, 7th Edition*, vols. 1-3, The Cosmetic, Toiletry, and Fragrance Association, Washington, DC; title page, publication page, and table of contents (1997).

Zushun et al., "The Inverse Emulsion Polymerization of Acrylamide Using Poly(Methyl Methacrylate)-Graft-Polyoxyethylene as the Stabilizer," *Journal of Applied Polymer Science*, 79:528-534 (2001).

ICI Companies Datasheet, "ICI Surfactants Arlacel® P135 Polymeric Emulsifier," 1 page total (published prior to Sep. 28, 2001).

U.S. Appl. No. 11/242,314, filed Oct. 3, 2005, Scholz et al.

* cited by examiner

WATER-IN-OIL EMULSIONS WITH ETHYLENE OXIDE GROUPS, COMPOSITIONS, AND METHODS

CROSS REFERENCE TO RELATED APPLICATIONS

This application is a continuation of U.S. patent application Ser. No. 09/966,511, filed Sep. 28, 2001, which has issued as U.S. Pat. No. 7,030,203

TECHNICAL FIELD

This invention relates to water-in-oil emulsions, compositions containing such emulsions, and methods. The emulsions can be used in moisturizing compositions (e.g., moisturizing skin treatments) to which medical adhesives will adhere, in tissue antiseptic preparations, in personal care compositions such as cosmetics, and in drug delivery compositions, for example. Such emulsions are preferably stable and substantive to mammalian tissue, typically skin.

BACKGROUND

Most of the moisturizing lotions and ointments commonly used to treat and protect mammalian skin consist of oil-in-water emulsions and creams, water-in-oil emulsions and, to a lesser degree, simply oil-based formulations. The oils used are selected from a large group of cosmetically accepted oils, which are generally recognized by the cosmetic industry for use on skin. Preferred oils have emollient properties. As a whole, these products either do not allow or do not enhance the ability of adhesive products, such as medical tapes, to adhere to skin to which they have been applied.

It is known that certain oil-soluble acrylate polymers, alone or in combination with conventional moisturizing oils, in oil-in-water or water-in-oil emulsions, provide skin treatments. For example, oil-soluble acrylate polymers have been used in sunscreening compositions of the water-in-oil type to reduce removal of the sunscreening agent from the skin by swimming or perspiration; in skin moisturizing compositions; with medicaments for topical application to the skin; in mosquito repellent compositions; and in cosmetic compositions such as lip rouges, mascaras, and eyeliners. Such skin treatments that are substantive (i.e., they are not readily removed by simple abrasion or water assault) are particularly desirable.

Water-in-oil emulsion compositions for skin treatment containing low molecular weight oil-soluble acrylate copolymers as emulsifying agents are disclosed in U.S. Pat. No. 4,552,755 (Randen et al.) and U.S. Pat. No. 6,200,596 (Swartzmiller). When these oil-soluble acrylate polymers are used with emollient oils in oil-in-water or water-in-oil emulsions, the result is a skin treatment that provides long lasting skin moisturizing effects. Also, unexpectedly, these compositions enhance (or do not significantly inhibit) the ability of pressure sensitive adhesives to adhere to treated skin. These polymers are prepared from carboxylic acid functional monomers such as acrylic acid, which until the present invention were believed to be important for adhesion of pressure sensitive adhesives. Such products are considered to have high substantivity on tissue.

U.S. Pat. No. 4,172,122 (Kubik et al.) teaches that carboxylic acid functional monomers such as acrylic acid are important in preparing acrylate polymers that can be used in products such as sunscreening products to reduce removal of the sunscreening agent from the skin by swimming or perspiration. Such products are considered to have high substantivity on tissue.

It has also been the conventional belief that carboxylic acid functional monomers, such as acrylic acid, were important for preparing stable water-in-oil emulsions. There is a desire, however, to eliminate such acidic components in products used on skin, particularly because they can deactivate antimicrobial agents, for example. Furthermore, it has been found that the carboxylic acid functional polymers are typically not capable of stabilizing water-in-oil emulsions at low pH, e.g., pH of less than about 5 and especially less than about 4.5. Thus, there is a need for water-in-oil emulsions that are preferably stable over a broad range of pH (e.g., about 3 to about 12) and that preferably do not include acidic components.

SUMMARY OF THE INVENTION

According to the present invention, there is provided a water-in-oil emulsion, preferably a stable water-in-oil emulsion. The water-in-oil emulsion includes a vinyl polymer, an oil phase, and a water phase. The vinyl polymer preferably provides moisturizing properties, substantivity, and adhesion enhancement (or adhesion non-inhibiting) treatments for mammalian (preferably, human) tissue (typically skin, as well as other tissues such as mucosal tissue and hair).

In one embodiment, the invention provides a water-in-oil emulsion that includes: a vinyl polymer including ethylene oxide-containing side chains and alkyl-Y-containing side chains, wherein Y is O or NR, wherein R is H or $CH_3$, and wherein the alkyl group of the alkyl-Y-containing side chain has at least 4 carbon atoms on average in a cyclic, branched-, or straight-chain configuration and optionally includes one or more heteroatoms; an oil phase; and a water phase. Preferably, the vinyl polymer includes ethylene oxide-containing side chains and alkoxy-containing side chains, wherein the alkyl group of the alkoxy-containing side chain has 4 to 50 carbon atoms on average in a cyclic, branched-, or straight-chain configuration and optionally includes one or more heteroatoms.

More preferably, the vinyl polymer is the reaction product of monomers including: at least one monoethylenically unsaturated alkyl(meth)acrylate monomer having the formula:

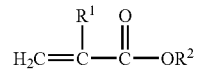

wherein: $R^1$ is H or $CH_3$; and $R^2$ is a linear, branched, or cyclic alkyl group optionally including one or more heteroatoms; and at least one monoethylenically unsaturated poly(alkylene oxide) (meth)acrylic monomer having the formula:

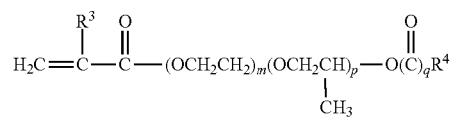

wherein: m is at least 2; p is 0 to 50; q is 0 or 1; $R^3$ is H or $CH_3$; and $R^4$ is hydrogen or linear or branched alkyl and/or aryl groups; with the proviso that the isopropylene oxide groups (the "p" groups) and the ethylene oxide groups (the "m" groups) are arranged in a reversed, alternating, random, or block configuration. Preferably, the vinyl polymer includes no more than about 0.1 wt-% copolymerized acidic monomers, typically, carboxylic acid monomers.

Preferably, about 60 percent by weight (wt-%) to about 90 wt-% of the monoethylenically unsaturated alkyl(meth)acrylate monomer and about 10 wt-% to about 40 wt-% of at least one monoethylenically unsaturated poly(alkylene oxide) (meth)acrylic monomer are used to prepare the vinyl polymer.

In another embodiment, the present invention provides a water-in-oil emulsion (preferably, at a pH of about 3 to about 5) that includes a polyetherpolyester emulsifying polymer; a water phase; and an oil phase; wherein the polyetherpolyester emulsifying polymer has the following structure:

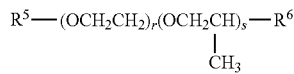

wherein: r is 10 to 200; s is 0 to 150; $R^5$ and $R^6$ are independently selected from polyester polymers or oligomers formed by the condensation polymerization of $C_8$-$C_{22}$ hydroxyalkyl acids wherein the polyester has at least 3 repeating units (i.e., groups) on average; with the proviso that the isopropylene oxide groups (the "s" groups) and the ethylene oxide groups (the "r" groups) are arranged in a reversed, alternating, random, or block configuration. Preferably, the polyetherpolyester polymer is a polyethylene oxide terminated in polyhydroxy stearate.

The present invention also provides moisturizing compositions, tissue antiseptic compositions (i.e., tissue disinfectants), personal care compositions, and transdermal drug delivery compositions that include one or more of the water-in-oil emulsions of the present invention. The tissue antiseptic compositions further include one or more antimicrobial agents and the transdermal drug delivery compositions further include one or more pharmaceutical agents.

The present invention also provides methods of using such compositions. These include, methods of moisturizing mammalian skin, methods of disinfecting mammalian tissue (e.g., skin or mucosal tissue), and methods of delivering a pharmaceutical agent to a mammal.

As used herein:

"water-in-oil emulsion" refers to a water-in-oil mixture in which the oil forms a continuous phase and the water is in discontinuous droplets. A water-in-oil emulsion can be distinguished from an oil-in-water emulsion by using an electrical emulsion tester according to the method described in the Examples Section. An oil-in-water emulsion will conduct electricity with relatively low resistance since water forms its external or continuous phase, whereas a water-in-oil emulsion will not conduct, or very poorly conduct, electricity;

"stable" as it relates to an emulsion means that the emulsion will have no visible water separation following one (preferably, two, and more preferably, three) freezing/thawing/centrifuging cycles according to the Emulsion Stability Test Protocol as described in the Examples Section;

"oil phase" in a water-in-oil emulsion refers to all components in the formulation that individually exceed their solubility limit in the water phase; these are materials that generally have solubilities of less than 1% in distilled water, however, water phase components such as salts may decrease the solubility of certain oils resulting in their partitioning into the oil phase;

"water phase" in a water-in-oil emulsion refers to the water present and any components that are water soluble, i.e., have not exceeded their solubility limit in water;

"substantivity" as it relates to an emulsion means that the emulsion can generally resist removal from mammalian tissue (typically skin) by water or abrasion, preferably, a substantive emulsion imparts barrier properties (i.e., resists contamination from external liquids) to mammalian tissue (typically skin);

"pressure sensitive adhesive" or "PSA" refers to a viscoelastic material that displays aggressive tackiness and adheres well to a wide variety of substrates after applying only light pressure (e.g., finger pressure). One well-known means of identifying pressure sensitive adhesives is the Dahlquist criterion. This criterion defines a pressure sensitive adhesive as an adhesive having a 1 second creep compliance of greater than $1 \times 10^{-6}$ square centimeters per dyne ($cm^2$/dyne) as described in *Handbook of pressure Sensitive Adhesive Technology*, Donatas Satas (Ed.), $2^{nd}$ Edition, p. 172, Van Nostrand Reinhold, New York, N.Y., 1989;

"(meth)acrylate monomers" are acrylic acid esters or methacrylic acid esters of alcohols;

"poly(alkylene oxide) monomers" are used interchangeably herein with poly(alkylene glycol) monomers and refer to ethylenically unsaturated poly(alkylene oxides);

"polymer" includes homopolymers and copolymers of any length; and

"copolymer" includes a polymer of any length (including oligomers) of two or more types of polymerizable monomers, and therefore includes terpolymers, tetrapolymers, etc., which can include random copolymers, block copolymers, or sequential copolymers.

DETAILED DESCRIPTION OF PREFERRED EMBODIMENTS OF THE INVENTION

Emulsions of the present invention include a vinyl polymer (i.e., a polymer derived from vinyl-containing monomers, typically monoethylenically unsaturated monomers) with ethylene oxide-containing side chains and alkyl-Y-containing side chains, wherein Y is O or NR, wherein R is H or $CH_3$; an oil phase; and a water phase. That is, the alkyl-Y-containing side chain can be an alkyl-O group (i.e., an alkoxy moiety) or an alkyl-NR group (i.e., an alkylamino moiety). Preferably, the alkyl groups of the alkyl-Y-containing side chains have at least 4 carbon atoms (on average) in cyclic, branched-, or straight-chain configuration, optionally substituted in or on the chain by heteroatoms (e.g., N, O, or S). The ethylene oxide groups and alkyl-Y groups can be, if desired, in the same side chains such that the ethylene oxide groups are terminated by alkyl-Y groups. As used herein, a "side chain" or "branch" relative to a "backbone" or "main chain" is a group of two or more atoms that branch off from the straight chain of carbon atoms formed by the vinyl polymerization.

Such emulsions are surprisingly stable as a result of the ethylene oxide-containing side chains in the vinyl polymer. This is surprising since acidic monomers such as acrylic acid are not necessarily needed to prepare the vinyl polymer. Such acrylic acid monomers have been traditionally believed to be necessary for such stability. Preferably, the vinyl polymer includes at least four ethylene oxide units (i.e., groups) in the ethylene oxide-containing side chains. Optionally, the vinyl polymer also includes isopropylene oxide units in the side chains.

Preferably, the vinyl polymers used in the emulsions of the present invention include little or no copolymerized acidic monomers such as ethylenically unsaturated carboxylic acids. That is, preferably, there are no acidic monomers intentionally added to the copolymerizable mixture, although small amounts can be present as impurities in other monomers. Thus, the polymer can include, for example, up to about (i.e., no more than about) 0.1 percent by weight (wt-%) copolymerized acidic monomers (typically, carboxylic acid monomers), based on the total weight of the vinyl polymer.

The vinyl polymers of the present invention include, for example, polymers derived from vinyl monomers such as (meth)acrylates, (meth)acrylamides, vinyl ethers, vinyl acetates and their hydrolyzed derivatives, styrenic compounds (i.e., derivatives of styrene), and N-vinyl lactams (including, for example, N-vinyl pyrrolidone, N-vinyl caprolactam, and their derivatives). Suitable vinyl polymers are soluble (i.e., form transparent homogenous solutions) or dispersible in the oil phase and tend to be insoluble or sparingly soluble in the water phase. Preferred vinyl polymers are soluble in the oil phase. Certain vinyl polymers are terpolymers.

A preferred class of polymers useful in the water-in-oil emulsions of the invention include polymers derived from the polymerization of at least one monoethylenically unsaturated alkyl(meth)acrylic monomer, preferably, an alkyl(meth)acrylic acid ester (i.e., an alkyl acrylate or alkyl methacrylate), wherein the alkyl group has at least 4 carbon atoms (on average) and no greater than 22 carbon atoms (on average), and at least one monoethylenically unsaturated poly(alkylene oxide) monomer, preferably, a monoethylenically unsaturated poly(alkylene oxide) (meth)acrylic monomer. Depending on the properties of the resultant polymer, the monoethylenically unsaturated alkyl (meth)acrylic acid esters used to prepare the polymer can have just short alkyl groups (e.g., at least 4 carbon atoms (on average) and no greater than 14 carbon atoms (on average)), or just long alkyl groups (e.g., at least 15 carbon atoms (on average) and no greater than 22 carbon atoms (on average)), or mixtures of monoethylenically unsaturated alkyl(meth)acrylic acid esters with short alkyl groups can be used in combination with monoethylenically unsaturated alkyl (meth)acrylic acid esters with long alkyl groups (e.g., terpolymers).

Alkyl(Meth)acrylic Monomers

One preferred class of vinyl polymers used in the emulsions of the present invention contains at least one copolymerized monoethylenically unsaturated alkyl(meth)acrylic monomer. As used herein, the "monoethylenically unsaturated" term in the alkyl(meth)acrylic monomer refers to the acrylic unsaturation. Preferably, "alkyl(meth)acrylic" monomers include (meth)acrylamides (e.g., octylacrylamide), (meth)acrylates, and combinations thereof. More preferably, the alkyl(meth)acrylic monomer is an alkyl(meth)acrylic acid ester (i.e., an alkyl acrylate or alkyl methacrylate), wherein the alkyl group has at least 4 carbon atoms (on average). Preferably, the alkyl group has no greater than 50 carbon atoms, more preferably, no greater than 36 carbon atoms, and most preferably, no greater than 22 carbon atoms (on average). Alternatively stated, these alkyl(meth)acrylate monomers are (meth)acrylic acid esters of alkyl alcohols (preferably, nontertiary alkyl alcohols), the alkyl groups of which preferably include, 4 to 22 carbon atoms (on average). Of these, one preferred alkyl group includes 4 to 14 carbon atoms, and more preferably 6 to 8 carbon atoms (on average). Another preferred alkyl group includes 14 to 22 carbon atoms, and more preferably 18 to 20 and carbon atoms (on average). The alkyl group can optionally contain heteroatoms and can be linear, branched, or cyclic.

Preferred alkyl(meth)acrylate monomers have the following general Formula (I):

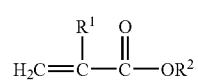

Formula (I)

wherein $R^1$ is H or $CH_3$, the latter corresponding to where the (meth)acrylate monomer is a methacrylate monomer, and $R^2$ is broadly selected from linear, branched, or cyclic alkyl groups and optionally includes one or more heteroatoms (e.g., N, O, or S). The number of carbon atoms in the $R^2$ group is as outlined above for the alkyl group of the alkyl-Y group (e.g., alkoxy group).

Examples of suitable alkyl(meth)acrylate monomers having shorter alkyl groups useful in the present invention include, but are not limited to, n-butyl acrylate, decyl acrylate, 2-ethylhexyl acrylate, hexyl acrylate, isoamyl acrylate, isodecyl acrylate, isononyl acrylate, isooctyl acrylate, lauryl acrylate, 2-methylbutyl acrylate, 4-methyl-2-pentyl acrylate, ethoxy ethoxyethyl acrylate, isobornyl acrylate, and the like. Particularly preferred of these are n-butyl acrylate, 2-ethylhexyl acrylate, isooctyl acrylate, lauryl acrylate, and mixtures thereof.

Examples of suitable alkyl(meth)acrylate monomers having longer alkyl groups useful in the present invention include, but are not limited to, stearyl acrylate, stearyl methacrylate, behenyl acrylate, acrylate esters of $C_{14}$-$C_{32}$ Gerbet alcohols, and the like. Particularly preferred of these is stearyl methacrylate. Various combinations of monoethylenically unsaturated alkyl (meth)acrylate monomers can be used in the emulsions of the present invention.

Preferably, the monoethylenically unsaturated alkyl(meth)acrylic monomer(s) can be used in an amount of at least about 60 weight percent (60 wt-%), and more preferably, at least about 75 wt-%, based on the total weight of the polymerizable composition. Preferably, the monoethylenically unsaturated alkyl(meth)acrylic monomer(s) can be used in an amount of no greater than about 90 wt-%, and more preferably, no greater than about 85 wt-%, based on the total weight of the polymerizable composition.

Poly(alkylene oxide) Monomers

One or more monoethylenically unsaturated poly(alkylene oxide) monomers can be copolymerized with the alkyl(meth)acrylic monomer(s). The monoethylenically unsaturated poly(alkylene oxide) monomers are selected for use in the emulsions such that they improve emulsion stability. Preferred monoethylenically unsaturated poly(alkylene oxide) monomers are monoethylenically unsaturated poly(alkylene oxide) (meth)acrylic monomers.

Particularly preferred monoethylenically unsaturated poly(alkylene oxide) monomers have the following general Formula (II):

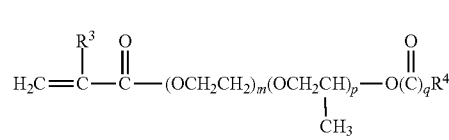

Formula (II)

wherein: m is at least 2; p is 0 to 50; q is 0 or 1; $R^3$ is H or $CH_3$, and $R^4$ is hydrogen or linear or branched alkyl and/or aryl groups. In this representation, the isopropylene oxide groups (the "p" groups) and the ethylene oxide groups (the "m" groups) can be arranged in a reversed, alternating, random, or block configuration. In any one monomer, m is preferably at least about 4. Preferably, m is no greater than about 115, more preferably, no greater than about 45, and most preferably, no greater than about 25. Preferably, p is 0. Preferably, q is 0. The $R^4$ group preferably includes at least 1 carbon atom, on average. The $R^4$ group preferably includes no more than 50 carbons, on average, more preferably, no more than 22 carbons, on average, and most preferably, is methyl.

Preferably, the monoethylenically unsaturated poly(alkylene oxide) monomers are poly(ethylene oxide) monomers or poly(ethylene oxide/propylene oxide) monomers. A particularly preferred such monomer is poly(ethylene oxide) monomer. The poly(ethylene oxide/propylene oxide) monomers can be random, sequential, or block. Examples of useful monoethylenically unsaturated poly(alkylene oxide) monomers include, but are not limited to, acrylate-terminated poly(ethylene oxide), methacrylate-terminated poly(ethylene oxide), methoxy poly(ethylene oxide) methacrylate, butoxy poly(ethylene oxide) methacrylate, acrylate-terminated poly(ethylene glycol), methacrylate-terminated poly(ethylene glycol), poly(ethylene oxide) diacrylate, poly(ethylene oxide) dimethacrylate, and combinations thereof.

Suitable poly(alkylene oxide) monomers include acrylate and methacrylate esters prepared from mono-hydroxyl-terminated poly(lower alkylene oxides) such as polyethylene and polypropylene glycols commercially available under the trade designation CARBOWAX from Union Carbide Corp. in a variety of molecular weights (e.g., CARBOWAX 350, CARBOWAX 550, CARBOWAX 750, CARBOWAX 2000, and CARBOWAX 5000); and their corresponding alkyloxy-terminated derivatives. Examples of suitable poly(alkylene oxide) monomers include those commercially available under the trade designations CD 550 (methoxy polyethylene glycol (350) monomethacrylate), and CD 552 (methoxy polyethylene glycol (550) monomethacrylate), all of which are available from Sartomer Chemicals, Exton, Pa.; and those commercially available under the trade designations M90G (methoxy polyethylene glycol (about 9 ethyleneoxy units) monomethacrylate) and M230G (methoxy polyethylene glycol (about 23 ethyleneoxy units) monomethacrylate), all of which are available from Shin-Nakamura Chemicals, Wakayama City, Japan; and those commercially available as poly(ethyleneglycol) methyl ether methacrylate (available with molecular weights of approximately 300, approximately 475, and approximately 1100) from Sigma-Aldrich, St. Louis, Mo. An example of a poly(alkylene oxide) monomer that also includes a long chain alkyl group is behenyl PEG-25 methacrylate commercially available as SIPOMER BEM from Rhodia, Cranbury, N.J. Preferred poly(alkylene oxide) monomers include poly(ethylene glycol) methyl ether methacrylate (with molecular weights of approximately 300, approximately 475, and approximately 1100). Various combinations of monoethylenically unsaturated poly(alkylene oxide) monomers can be used in the emulsions of the present invention.

Preferably, the monoethylenically unsaturated poly(alkylene oxide)monomer(s) can be used in an amount of at least about 10 wt-%, based on the total weight of the polymerizable composition. Preferably, the monoethylenically unsaturated poly(alkylene oxide) monomer(s) can be used in an amount of no more than about 40 wt-%, based on the total weight of the polymerizable composition.

Preparation of the Vinyl Polymer

The preparation of the vinyl polymers from monomers of the type disclosed herein is well documented in the literature and can be carried out by free radical initiated bulk, solution, precipitation, suspension or emulsion techniques. Generally, the solution technique is preferred. Specific polymerization methods used in this invention are discussed in the Examples Section.

Generally for the solution polymerization technique, the monomers are dissolved in a suitable solvent, a free radical initiator is added, the solution is purged with inert gas (nitrogen) to remove oxygen, and the initiator is activated. The amount of solvent is generally about 30 wt-% to about 80 wt-%, based on the total weight of the reactants and solvents. Generally the initiator is present in an amount of about 0.005 part to about 1 part based on 100 parts of total monomer. Activation of the initiator may be by thermal decomposition, radiation induced decomposition, or by chemical reaction via a redox couple. Thermally activated initiators are most preferred.

Usually the solution is agitated during the reaction to mix the components. Optionally, a chain transfer agent may be added to the reaction to regulate the molecular weight of the polymer product. The monomer conversion may vary depending on the viscosity of the reaction solution and the reaction temperature. Typically, monomer conversion of 98 percent or greater is obtained within 48 hours. Suitable solvents for the polymerization reaction may be any organic liquid that is inert to the reactants and product and will not otherwise adversely affect the reaction. Such solvents include alcohols, esters, ketones, aliphatic or aromatic hydrocarbons, and mixtures thereof. The reaction may be done in a relatively low boiling solvent, and after the reaction is complete the product may be exchanged into the higher boiling emollient oil solvent by adding the emollient oil to the reaction mixture and evaporating the lower boiling reaction solvent under reduced pressure. The emollient oils may optionally be used as reaction solvents for the polymerization.

Polymerization Initiators. A free radical initiator is preferably added to aid in the copolymerization of (meth)acrylate and various comonomers. The type of initiator used depends on the polymerization process. Suitable initiators include photoinitiators, thermal initiators, redox initiators, etc. Photoinitiators that are useful for polymerizing the polymerizable mixture of monomers include benzoin ethers such as benzoin methyl ether or benzoin isopropyl ether, substituted benzoin ethers such as 2-methyl-2-hydroxypropiophenone, aromatic sulfonyl chlorides such as 2-naphthalenesulfonyl chloride, and photoactive oxides such as 1-phenyl-1,1-propanedione-2-(O-ethoxycarbonyl)oxime. An example of a commercially available photoinitiator under the trade designation IRGACURE 651 is 2,2-dimethoxy-1,2-diphenylethane-1-one (commercially available from Ciba-Geigy Corp.). Examples of suitable thermal initiators include those available under the trade designations VAZO-64 (2,2'-azobis(isobutyronitrile) and VAZO-67 (2,2'-azobis(2-methylbutanenitrile), both of which are available from DuPont Co., hydroperoxides, such as tert-butyl hydroperoxide, and peroxides, such as benzoyl peroxide and cyclohexane peroxide. Examples of suitable redox initiators, such as tert-butyl hydroperoxide plus a reducing agent (e.g., tertiary amines, ferrous sulfate, sodium formaldehyde sulfoxylate, and sodium bisulfite).

Polymerization Chain Transfer Agents. Optionally, the composition also includes a chain transfer agent to control the molecular weight of the polymerized compositions. Chain transfer agents are materials that regulate free radical polymerization and are generally known in the art. Suitable chain transfer agents include halogenated hydrocarbons such as carbon tetrabromide, and sulfur compounds such as lauryl mercaptan, butyl mercaptan, ethanethiol, isooctylthioglycolate (IOTG), 2-ethylhexyl thioglycolate, 2-ethylhexyl mercaptopropionate, 2-mercaptoimidazole, and 2-mercaptoethyl ether and mixtures thereof. The amount of chain transfer agent that is useful depends upon the desired molecular weight and the type of chain transfer agent. The chain transfer agent is typically used in amounts from about 0.001 part to about 10 parts by weight per 100 parts of total monomer. Alternatively, the solvent (e.g., ethanol, isopropanol) could serve as the chain transfer agent.

Emulsion Formulation and Preparation

The molecular weight of the polymers used in the compositions may vary over a broad range. The molecular weight is preferably suitably large to provide the requisite binding effect between a coating composition containing the emulsion and an adhesive applied over the coating composition. The upper limit is determined largely by formulation requirements. As the molecular weight increases, the polymers tend to become too viscous to formulate easily into cosmetically appealing compositions. Preferably, the vinyl polymers have an inherent viscosity (in units of deciliters per gram (dl/g)) of at least about 0.2, more preferably, at least about 0.4, and preferably, no greater than about 3.0, more preferably, no greater than about 2.0, when measured at 0.30 wt-% of the polymer in tetrahydrofuran.

Preferably, the vinyl polymers have a calculated hydrophilic-lipophilic balance (HLB) of more than about 1, and more preferably, at least about 1.5. Preferably, the vinyl polymers have a calculated HLB of less than about 10, and more preferably, no more than about 6.5. The HLB value is calculated by dividing the total weight percent of ethylene oxide units in the polymer by 5. For systems involving more than one vinyl polymer the HLB is calculated as a weight average value. For example, in a system comprising 40% by weight of a vinyl polymer having an HLB of 5 and 60% of a vinyl polymer having an HLB of 4 the weight average HLB for the system is 4.4. The preferred HLB range may vary somewhat depending on the length of the polyethylene oxide side chain. Generally for polymers based on PEG 475, polymers with HLB values less than 1 do not produce emulsions and polymers with HLB values greater than 8 may produce emulsions, but the stability of the emulsions is poor. Polymers with longer ethylene oxide-containing side chains may form stable emulsions over a wider range of calculated HLB values and polymers with shorter ethylene oxide-containing side chains may have a narrower range. The HLB may also vary depending on the oil phase components, e.g., more polar oils may require higher HLB polymers. Also, the preferred range of HLB values may vary depending on other additives, which may optionally be added to the emulsion formulation. For example, addition of magnesium sulfate to the formulation may result in a broader useful range of HLB values for particular polymers with a given ethylene oxide-containing side chain compared to formulations without added magnesium sulfate.

One or more vinyl polymers are preferably present in an emulsion of the present invention in a total amount of at least about 0.25 wt-%, and more preferably, at least about 0.5 wt-%, based on the total weight of the emulsion. One or more vinyl polymers are preferably present in an emulsion of the present invention in a total amount of no more than about 10 wt-%, and more preferably, no more than about 3 wt-%, based on the total weight of the emulsion.

The oil used in the emulsions of the present invention can be selected from a wide variety of oils or mixtures of oils that are conventionally used in the cosmetic art. Preferably, the oil is an "emollient oil" which as used herein refers to any dermally acceptable oil or mixture of oils which forms a barrier on the skin capable of retarding the evaporation of water from the skin. The oil base of the emulsions can be solid or liquid, but the entire formulation should be somewhat fluid at skin temperatures for ease of application.

Examples of suitable oils include silicone fluids, saturated fatty esters and diesters such as diisopropyl adipate, dicapryl adipate, diisopropyl sebacate, dioctyl sebacate, dioctyl ether, glyceryl tricaprylate/caprate, diethyleneglycol dicaprylate/caprate, propylene glycol dipelargonate, polyalkoxylated alcohols such as 15 mole propoxylate of stearyl alcohol, paraffin oils and waxes, animal and vegetable oils including mink oil, coconut oil and derivatives thereof, palm oil, corn oil, cocoa butter, petrolatum, coconut oil, sesame oil, and the like, lanolin derivatives, fatty alcohols such as isostearyl alcohol, isocetyl alcohol, cetyl/stearyl alcohol, and straight chain alcohols from $C_6$-$C_{18}$ and certain petroleum distillates which are toxicologically safe such as $C_8$-$C_{22}$ isoparaffin hydrocarbon solvents, e.g., isooctane and isododecane. Other oils are water insoluble esters such as short chain esters of long chain alcohols or acids. Examples include methyl behenate, methyl stearate, arachidyl propionate, behenyl lactate, stearyl acetate, isopropyl palmitate, 2 mole propoxylate of myristyl propionate, isopropyl myristate, cetyl palmitate, butyl stearate, and glycerol monoerucate. The oils mentioned in this list are merely examples and are not intended to limit the invention in any way.

Oils that are particularly preferred in the practice of the present invention include isopropyl palmitate, coconut oil, isooctane, isododecane, petrolatum, cetyl palmitate, cetyl/stearyl alcohol, diethyleneglycol dicaprylate/caprate, diisopropyl sebacate, glyceryl tricaprylate/caprate, diiospropyl adipate, dicapryl adipate, silicone fluids, 2 mole propoxylate of myristyl propionate, and 15 mole propoxylate of stearyl alcohol (e.g., that commercially available under the trade designation ARLAMOL E from Uniqema, Wilmington, Del.).

Preferably, one or more oils (in the oil phase) used in the emulsions of the present invention are present in a total amount of at least about 20 wt-%, more preferably, at least about 30 wt-%, and most preferably, at least about 40 wt-%, based on the total weight of the emulsion. Preferably, one or more oils used in the emulsions of the present invention are present in a total amount of no more than about 80 wt-%, more preferably, no more than about 70 wt-%, and most preferably, no more than about 60 wt-%, based on the total weight of the emulsion.

The emulsions preferably include at least about 15 wt-% water, more preferably, at least about 30 wt-% water, and most preferably, for certain embodiments, such as for creams and lotions, the emulsions include at least about 40 wt-% water, based on the total weight of the emulsion. They preferably include no more than about 70 wt-% water, and more preferably, no more than about 55 wt-% water, based on the total weight of the emulsion.

The water-in-oil emulsions are generally prepared by heating, independently, the oil phase (containing the vinyl polymer and optional ingredients, e.g., surfactants) and the water phase (containing optional ingredients, e.g., humectants and stabilizers), and slowly adding the water phase to the oil phase with good agitation. Homogenization is preferred, but it is not necessary. Upon cooling, other optional ingredients may be added, e.g., skin barrier/protectant materials, preservatives, and thickeners.

Preferred emulsions of the present invention have substantivity properties when applied to skin and thus are able to resist water and/or abrasive removal and act as a barrier to external liquid challenges, such as from potential skin contaminants such as urine, blood, and feces. The degree of substantivity can be measured in one instance by the Substantive Barrier Function Test Protocol as described in the Examples Section. Briefly, skin is treated with an emulsion sample, dried, soaked in water for 12 minutes, blotted dry, and the capacitance measured with a Novameter instrument. The results are compared to the capacitance of an untreated (control) portion of the skin. An emulsion having substantive barrier properties will reduce the amount of moisture penetrating the skin and the skin will have a reduced level of capacitance in comparison to the control. Preferably, an emulsion having a useful degree of substantivity will provide a reduction in skin capacitance of greater than about 15%, and more preferably, greater than about 20%.

Humectants are also advantageously incorporated into the water phase of the compositions of the present invention. As used herein the term "humectant" refers to polar compounds or mixtures of compounds that act to retain or absorb moisture. Suitable humectants include, but are not limited to, polyols, such as glycerin, propylene glycol, dipropylene glycol, polypropylene glycol, glycerine ethoxylates, methyl glucose ethoxylates, polyethylene glycol, polyethylene/polypropylene glycols, and sorbitol. Dipropylene glycol and polypropylene glycol are particularly preferred humectants.

The addition of low levels of stabilizing ingredients in the water phase can also be advantageous. Salts such as magnesium sulfate may be useful emulsion stabilizers, and they do not significantly affect the water resistance of the formulations. However, the addition of magnesium sulfate can, in some instances, inactivate bioactive agents, e.g., antimicrobial agents such as chlorhexidine gluconate. The addition of water-soluble gums such as guar derivatives, xanthan gum, and thickeners such as hydroxy ethyl cellulose, hydroxy propyl cellulose and carboxyl vinyl polymers may be helpful in stabilizing the emulsion. Oil phase emulsion stabilizers include ethylene/acrylic acid copolymer such as an ethylene/acrylic acid copolymer available under the trade designation AC540 from Allied Signal, Morrison, N.J., N-vinyl pyrrolidone/olefin copolymers such as that available under the trade designation GANEX V-216 from ISP International Specialty Products, Wayne, N.J.

The addition of silicone oil dimethicone to the oil phase prior to preparation of the emulsion can also be advantageous in improving the ability of the emulsions to act as a barrier to urine, feces, or other indigenous and exogenous materials when used as moisturizing compositions (e.g., moisturizing skin treatments) and other personal care compositions. The dimethicone may be present in concentrations up to about 5 wt-% and preferably are present in concentrations greater than about 1.0 wt-%, based on the total weight of the emulsion.

Auxiliary emulsifiers conventionally used in cosmetic formulations can be employed to ensure stability and extend shelf life of any of the compositions of the present invention. Such auxiliary emulsifiers are distinct from the vinyl polymers described herein, and typically function as surfactants. It has also been found that the auxiliary emulsifier can influence substantivity to some extent. Auxiliary emulsifiers that provide good substantivity include polyalkoxylated glyceryl $C_6$-$C_{22}$ alkyl esters such as 82-mole ethoxylate of glyceryl tallowate, glyceryl $C_6$-$C_{22}$ alkyl esters such as glyceryl stearate, $C_{12}$-$C_{18}$ alkyl carboxylic acids such as stearic acid, $C_{12}$-$C_{22}$ polyalkoxylates such as laureth-4, polypropylene glycol (PPG) (15) stearyl ether (commercially available under the trade designation ARLAMOL E from Uniqema, Wilmington, Del.), and 20-mole ethoxylate of cetyl/stearyl alcohol, polyetherpolyester polymers such as polyethylene glycol (PEG) (30) polyhydroxy-stearate, MW of approximately 5000 (commercially available under the trade designation ARLACEL P135 from ICI, Wilmington, Del.). The auxiliary emulsifier is preferably present in an amount of at least about 1 wt-%, more preferably, at least about 5 wt-%, and preferably, no more than about 20 wt-%, more preferably, no more than about 10 wt-%, based on the total weight of the emulsion.

Certain embodiments of the water-in-oil emulsion of the present invention include an emulsifying polyetherpolyester polymer, an oil phase, and a water phase. These emulsions do not necessarily include a vinyl polymer. Furthermore, these emulsions do not necessarily have desirable substantivity, but are suitable for applications not requiring substantivity such as beneath a medical article. These polyetherpolyester polymers are preferred for use in emulsions having a pH of about 3 to about 5 and/or in compositions containing an antimicrobial. Such compositions are useful, for example, in disinfecting mammalian skin.

The polyetherpolyester emulsifying polymer has the following Formula (III):

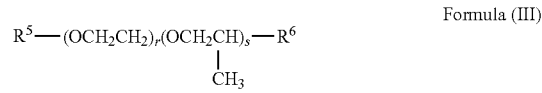

Formula (III)

wherein: r is 10 to 200, preferably, r is 10 to 100, and more preferably, r is 20 to 40; s is 0 to 150; and $R^5$ and $R^6$ are independently selected from polyester polymers or oligomers formed by the condensation polymerization of $C_8$-$C_{22}$ hydroxyalkyl acids, wherein the polyester has at least 3 repeating units on average. Preferably, the polyester has at least 4, and more preferably, at least 6 repeating units on average. In this representation, the isopropylene oxide groups (the "s" groups) and the ethylene oxide groups (the "r" groups) can be arranged in a reversed, alternating, random, or block configuration. A particularly preferred polyetherpolyester emulsifying polymer is polyethylene glycol polyhydroxy stearate having about 30 moles of polyethylene oxide and a total of 12 units of polyhydroxy stearate. An example is the material commercially available under the trade designation ARLACEL P135 from ICI, Wilmington, Del.

Certain emulsions of the present invention find particular utility as moisturizing skin treatments. Preferably, such skin treatments are substantive. They preferably are compatible with antimicrobial agents and do not typically adversely affect adhesion of pressure sensitive adhesive articles, as discussed in greater detail below.

Certain emulsions of the present invention find particular utility as presurgical and precatherization tissue (e.g., skin) antiseptics (i.e., disinfectants) and in general for disinfecting skin and mucosal tissue with an antimicrobial composition, which is preferably substantive. The preferred compositions are not only substantive but allow for immediate placement of adhesive products, such as medical tapes, surgical incise drapes or wound dressings, directly over the coated skin. The emulsions of this invention not only allow adhesion over these products but in many cases actually enhance the adhesion and may especially enhance the adhesion of these products in moist or wet conditions such as beneath a surgical incise drape exposed to body fluids and around a catheter or other percutaneous puncture.

The emulsions of the present invention are advantageously compatible (i.e., retain biological activity and emulsion stability) with at least one bioactive agent, whether incorporated into the emulsion or contacted by the emulsion. One test for compatibility is the Chlorhexidine Gluconate (CHG) Compatibility Test Protocol as described in the Examples Section. Bioactive agents typically include antimicrobials such as antibacterials, antivirals, antifungals, as well as corticosteroids such as hydrocortisone, and topical anesthetics.

A preferred bioactive agent is an antimicrobial. Examples of antimicrobial agents include iodine and its complexed forms, which are commonly referred to as iodophors. Iodophors are iodine complexes with polyethylene glycol and its derivatives, N-vinyl caprolactam containing polymers such as polyvinylpyrrolidone, as well as other polymers that tend to hydrogen bond with hydrogen iodide or hydrogen triiodide or complex with salts such as sodium or potassium triiodide. A particularly preferred iodophor is povidone-iodine and most preferably povidone-iodine USP. Other antimicrobials include chlorhexidine salts such as chlorhexidine gluconate (CHG); parachlorometaxylenol (PCMX); triclosan; hexachlorophene; fatty acid monoesters of glycerin and propylene glycol such as glycerol monolaurate, glycerol monocaprylate, glycerol monocaprate, propylene glycol monolaurate, propylene glycol monocaprylate, propylene glycol monocaprate; phenols; surfactants and polymers that include a $C_{12}$-$C_{22}$ hydrophobe and a quaternary ammonium group; polyquaternary amines such as polyhexamethylene biguanide; quaternary silanes; hydrogen peroxide; silver and silver salts such as silver chloride, silver oxide and silver sulfadiazine; and the like. The most preferred antimicrobial agent is chlorhexidine since it is capable of ensuring long term antimicrobial efficacy. If chlorhexidine is in or contacted by the emulsion of the present invention it is preferably a soluble salt. The diacetate and digluconate salts are preferred. The most preferred antimicrobial agent is chlorhexidine gluconate (CHG), also referred to as chlorhexidine digluconate. Various combinations of antimicrobial agents can be used in the emulsions of the present invention.

If added to an emulsion, one or more antimicrobial agents are preferably present at a level of at least about 0.05 wt-%, and more preferably, at least about 0.25 wt-%, based on the total weight of the emulsion. One or more antimicrobial agents are preferably present at a level of no greater than about 10.0 wt-%, and more preferably, no greater than about 8.0 wt-%, based on the total weight of the emulsion.

With certain additives, such as iodine and iodophors, it is highly desirable to formulate an emulsion having a low pH, e.g., about 3 to about 5. As previously discussed, there have been past reports of certain water-in-oil emulsions that contain polymers having carboxylic acid groups to stabilize the emulsions. It has been found that these carboxylic acid functional polymers do not form stable emulsions when formulated into emulsions typical of the prior art at low pH. While not being bound by theory we believe that stabilization is only achieved at elevated pH where the carboxylic acid groups are ionized. Typically, these polymers having carboxylic acid groups have a pKa value of about 4 to about 4.5 and thus at a pH of 4 most of the carboxylic acid groups would be protonated and incapable of contributing to stability, thereby resulting in unstable water-in-oil emulsions. Unlike these materials, the polymers of the present invention do not rely upon ionizable groups to ensure preferred emulsion stability. Rather, the stabilization is a result of the nonionic polyethylene oxide functional monomers incorporated into the polymers of the present invention. These nonionic groups contribute to emulsion stability over a broad pH range, e.g., about 2 to about 12.

It may also be suitable to add systemically active pharmaceutical agents to the water-in-oil emulsions of the present invention to produce transdermal drug delivery vehicles, which are preferably substantive. When applied to the skin the pharmaceutical agent would be transported across the skin into the bloodstream. In this regard it may be particularly appealing to add penetration enhancing agents particularly to the oil phase, such as lauryl alcohol, oleyl alcohol, lauramide DEA, lauryl pyrrolidone-5-carboxylate, and ascorbyl palmitate. Penetration enhancing agents such as glycerin, propylene glycol, and tetraglycol may also be added to the water phase. Other penetration enhancing agents, as well as exemplary pharmaceutical agents, that may be added to the water-in-oil emulsions of the present invention may be found in U.S. Pat. No. 6,086,911 (Godbey).

When applied to mammalian (preferably, human) skin (or other tissue such as mucosal tissue or hair), the emulsions of the present invention form an oil film on the tissue surface. Surprisingly, in spite of the oiliness and moisturizing effects of the emulsions, pressure sensitive adhesives, such as used on medical tapes, IV site dressings, and surgical incise drapes, adhere at least as well and, in most cases, more strongly to the emulsion-treated tissue (typically, skin) than to untreated tissue (typically, skin). Medical tapes and dressings that adhere particularly well to the emulsions include those utilizing acrylate, block copolymer (e.g., adhesives based on KRATON polymers commercially available from Kraton Polymers, Houston, Tex.) and rubber based pressure sensitive adhesives. Examples are tapes and dressings commercially available from 3M Company under the trade designations TRANSPORE, BLENDERM, STER1-STRIPS, MICROPORE, TEGADERM, STERIDRAPE, and IOBAN II.

A pressure sensitive adhesive article (e.g., tape, incise drape, wound dressing, and the like) applied over the emulsions (or compositions containing the emulsions) of the present invention on mammalian tissue, typically skin (after allowing the emulsion or composition containing the emulsion to dry for at least 15 seconds), preferably adheres at a level of at least about 50% of the level of adhesion of the pressure sensitive adhesive article applied directly to the tissue, typically skin (i.e., without the emulsion). This can be measured by applying a thin uniform amount of the emulsion to skin as described in the Examples Section, applying the adhesive article, and rolling with a 4.5-pound (2.1-kg) 2-inch (5.1-cm) wide roller. After waiting 1-5 minutes the adhesive article is removed at a peel angle of 180 degrees at a speed of 12 inches/minute (30.5 cm/minute). Due to the variability in skin types a statistically relevant sample is employed which is typically at least 8 subjects where at least 2 strips are applied to the backs of each subject.

The emulsions of this invention, if applied in a thin film to mammalian tissue, typically skin, preferably allow instantaneous adhesion of medical adhesive products. That is, typically and preferably, within about 60 seconds, and often, in as little as 15 seconds, of application of a thin film, an adhesive product can be applied over the composition that will exhibit good adhesion in as little as about 5 minutes, preferably as little as about 60 seconds, and most preferably in as little as about 40 seconds. In many of the preferred cases the adhesion over the compositions of the present invention will exceed that of the product applied to dry unprepared tissue (typically skin).

The oil phase used in the water-in-oil emulsions of the present invention are preferably compatible with the medical pressure sensitive adhesives that may be placed over the composition. Not all oils will be compatible (i.e., allow good adhesion of the article) with all adhesives. For polyacrylate-based pressure sensitive adhesives, the oil phase preferably contains an ester-functional emollient oil or other emollient oil that is capable of plasticizing the adhesive, such as those described in U.S. Pat. No. 5,951,993 (Scholz et al.). For example, with most pressure sensitive adhesives that include predominantly alkyl acrylates, such as isooctylacrylate or 2-ethylhexylacrylate, emollient oils such as glyceryl tricaprylate/caprate, diiospropylsebacate, isopropylpalmitate, diisopropyl adipate, diethyleneglycoldioctanoate/diiosnonanoate, and the like, are very effective. Also preferred are certain ether-based emollient oils. For example, with most polyacrylate pressure sensitive adhesives that include predominantly isooctylacrylate or 2-ethylhexylacrylate, dimethylisosorbide and PPG2 methyl ether are effective. Preferably, the oil is not too polar. For example, materials such as glycereth 7 diisononanoate and glycerol triacetate may tend to reduce the adhesion of the medical pressure sensitive adhesive significantly. It should be noted, however, that minor amounts of more polar components may be added to the oil phase and still allow good drape adhesion.

Importantly, since the continuous phase of the emulsion is a water-insoluble oil, the adhesion of a medical adhesive product is not easily undercut by water or body fluids. This is particularly important for use of an emulsion as a presurgical tissue antiseptic ("prep"), for use on skin or mucosal tissue (preferably, skin), over which an incise drape is optionally applied. In these surgical applications blood, saline, and other body fluids are constantly present which may tend to wash water-soluble preps away and perhaps even into the wound. The water-in-oil emulsion preps of the present invention, however, resist wash off very well.

Furthermore, the water resistance is also important for preps over which an adhesive product is applied. For example, when using a surgical incise drape (adhesive coated film through which a surgical incision is made) adhesion to the composition throughout the surgery is important. Therefore, resistance to water and body fluid infiltration from the wound edge is important. This is similarly very important for use around percutaneous devices such as a catheter insertion site. These sites often have fluid build up around the catheter, which can affect adhesion. The adhesion of dressings such as thin film adhesive coated dressings over the compositions of the present invention ensures a strong bond despite the presence of moisture.

Another key advantage of the preferred emulsions of the present invention, which is particularly important for tissue antiseptics such as preoperative surgical preps and IV site preps, is that the emulsions may be removed gently with a cloth, gauze or other fabric optionally using a mild detergent for complete removal. No organic solvent-based removers are necessary but may be used if desired.

The emulsions of the present invention may be used to form milks (i.e., low viscosity emulsions similar in consistency to cow's milk), lotions, and creams that are preferably water-repellent, moisturizing, and long lasting compared to most other commercially available skin lotions. These features are important for ostomy or incontinence applications where protection of the skin from irritating body fluids such as urine, feces, and intestinal fluids is desired. The fact that the emulsions may enhance adhesion of pressure sensitive adhesives, allows them to be used to protect skin surrounding stomas, dermal ulcers, diseased skin, or surgical wounds without interfering with the application of adhesive wound dressings. This is also a major advantage over other percutaneous dressings when the present-invention emulsions are used in challenging fluid environments associated with surgical incise drapes, IV site dressings, and other dressings.

The emulsions of the present invention are useful in the preparation of various personal care compositions (e.g., cosmetic compositions), including hair care compositions such as styling agents (e.g., hair sprays, styling mousses, styling gels), shampoos, dyes, conditioners, rinses, and antidandruff preparations. Other personal care compositions include insect repellants, shaving products, hand and body lotions, gels, creams, moisturizers, sunless tanning compositions, cleansers, toners, astringents, fresheners, and masks for the hair and skin, polishes and strengtheners for the nails, underarm deodorants and antiperspirants, bath powders, talcs, bath oils, bubble baths, makeup products such as makeup for the eyes, cheeks, and lips, colognes, perfumes, compositions for cushioning sores, and hair removal compositions.

Examples of specific products that could especially benefit from having present the water-in-oil emulsions of the present invention, include but are not limited to, lipsticks (both solid and liquid at room temperature and which provide glossy or matte finish), eye shadows (both solid and liquid at room temperature and which provide glossy or matte finish), eye liners, mascara, rouge, face powder, foundation (both solid and liquid at room temperature and which provide glossy or matte finish), compositions for masking or camouflaging skin blemishes, sunscreens (organic, inorganic, or combinations thereof), and temporary hair coloring compositions (whole head, streaks and/or highlights).

Accordingly, in addition to the additives listed above, emulsions of the present invention may include other materials to provide therapeutic or protective cosmetic utility. Examples include conditioners, sunscreen agents, insect repellents, vitamins, herbal extracts, antiperspirant or deodorant agents, skin or hair bleaching or coloring agents including sunless tanning agents, depilating agents, antidandruff agents, antiacne agents, astringents, tensors, skin toning agents, or corn, callus, or wart removers. The emulsions also may include materials having decorative or color cosmetic utility, for example, by incorporation of glitter, pigments, dyes, bleaches, perfumes, or fragrances.

Other materials conventionally used in cosmetic compositions, such as preservatives, antioxidants, waxes, film-forming polymers, propellants, buffers, organic or inorganic suspending or thickening agents, plasticizers, herbal extracts, and flavoring agents can also be included in minor amounts of the emulsions of the present invention, preferably in amounts that do not adversely affect the substantivity of the compositions. These materials can be added to the aqueous or oil phase (depending on solubility) prior to emulsification, or added after the emulsions have been prepared and cooled. The latter is preferred when materials with heat sensitivity are used.

Preferred cosmetic preparations of the present invention do not transfer certain ingredients (such as coloring agents) from the surface applied, such as skin or hair, to unintended surfaces, such as clothing or upholstery. Such preferred cosmetic preparations are described as having transfer resistant or transfer proof properties.

The preferred water-in-oil emulsions can be prepared by conventional methods, such as slowly adding a heated water phase material to a heated oil phase material and agitating or homogenizing with a high-speed mixer. A specific cosmetic emulsion embodiment of the invention is provided in the Examples Section; however, it is well known to one skilled in the art that a variety of ingredients or combination of ingredients and active agents can be utilized to obtain a cosmetic formulation optimized for a particular utility or market segment. A typical reference source that lists standard cosmetic ingredients is the International Cosmetic Ingredient Dictionary and Handbook, published by The Cosmetic, Toiletry, and Fragrance Association, John A. Wenninger and G. N. McEwen, Jr., Editors, 7th Edition, 1997.

EXAMPLES

The objects, features, and advantages of the present invention illustrated in the following examples, which incorporate particular materials and amounts, should not be construed to unduly limit this invention. All materials are commercially available unless otherwise stated or apparent. All parts, percentages, ratios, etc., in the examples are by weight unless otherwise indicated.

GLOSSARY

| | |
|---|---|
| IOA | Isooctyl Acrylate |
| SMA | Stearyl Methacrylate (Rocryl 330, Rohm and Haas, Philadelphia, PA) |
| LMA | Lauryl Methacrylate (Rocryl 320, Rohm and Haas) |
| PEG475 | Poly(ethyleneglycol) Methyl Ether Methacrylate (Sigma-Aldrich, MW approximately 475) |
| EEEA | Ethoxyethoxy Acrylate (SR 256, Sartomer, Exton, PA) |
| PEG300 | Poly(ethyleneglycol) Methyl Ether Methacrylate (Sigma-Aldrich, MW approximately 300) |
| PEG1100 | Poly(ethyleneglycol) Methyl Ether Methacrylate (Sigma-Aldrich, MW approximately 1100) |
| IPP | Isopropyl Palmitate (Sigma-Aldrich Fine Chemicals, St. Louis, MO) |
| VAZO-67 | 2,2'-azobis(2-methylbutanenitrile) (Dupont, Wilmington, DE) |
| DIPS | Diisopropyl Sebacate (Alzo, Sayerville, NJ) |
| M90G | Poly(ethyleneglycol) Methyl Ether Methacrylate (Shin-Nakamura Chemicals, Wakayama City, Japan) |

Test Protocols

Inherent Viscosity (IV)

The inherent viscosity of a polymer is measured in accordance with the protocol described by Fred Bilmeyer, Jr. at pages 84-85 of the textbook entitled *Textbook of Polymer Science*, Second Edition, published by Wiley-Interscience (1971). Briefly, solution viscosity is measured by comparing the efflux time (t) required for a specified volume of polymer solution to flow through a capillary tube with the corresponding efflux time ($t_0$) for the solvent. The measured variables t, $t_0$, and solute concentration (c) are then used to calculate inherent viscosity (also know as Logarithmic Viscosity) using the equation:

$$\eta = (\ln t/t_0)/c$$

For the examples of the present invention, IV was determined as a 0.3 weight percent of the polymer in tetrahydrofuran (THF).

Hydrophilic-Lipophilic Balance (HLB)

In polymers containing only a single hydrophilic component, the HLB value was calculated as E/5, where E=the concentration in weight percent of the ethylene oxide units.

Emulsion Stability

A 10-milliliter (10-ml) sample of an emulsion (e.g., lotion or cream formulation) formulation was placed in a 15-ml conical-shaped graduated plastic centrifuge tube (Corning), frozen for approximately 2 hours at approximately −20° C., thawed to room temperature for approximately 2 hours, and centrifuged at 3,000 revolutions per minute (rpm) for 10 minutes using a Labofuge B, model 2650 manufactured by Heraeus Sepatech GmbH, Osterode, West Germany. This cycle of freezing/thawing/centrifuging was repeated for a total of three times. A stable formulation will have no visible water separation in the bottom of the tube.

Emulsion Conductivity Test

An emulsion sample was tested with an Electrical Emulsion Tester (EET) (EET information available from ICI Americas, Inc. Bridgewater, N.J.) in order to distinguish between a water-in-oil emulsion and an oil-in-water emulsion. An oil-in-water emulsion will conduct electricity since water includes its external or continuous phase, whereas a water-in-oil emulsion (free of conductive agents having solubility in the oil phase) will not conduct electricity. The EET consists of resistor electric contacts (30,000 ohm, 0.5 watt), a resistor neon lamp (56,000 ohm, Type NE-51), and a push-button switch all wired in series. To conduct the test, the electric contacts were placed into a sample of the emulsion and the push-button switch was turned on. The lamp would glow in the case of an oil-in-water emulsion and would not glow in the case of a water-in-oil emulsion (free of conductive agents having solubility in the oil phase).

Emulsion Dilution Test

An emulsion sample was tested in this Emulsion Dilution Test in order to distinguish between a water-in-oil emulsion and an oil-in-water emulsion in those cases where the former is suspected of containing conductive agents with solubility in the oil phase. For example, a water-in-oil emulsion containing povidone-iodine will have $I_2$ and $I_3^+$ units in the oil phase that can impart conductivity to the oil phase and thereby provide misleading results in the Emulsion Conductivity Test. The Emulsion Dilution Test was conducted according to the following procedure. A 2-ml sample of the emulsion was added at room temperature to 2 ml of deionized water. The emulsion was gently stirred and observed. If the resulting emulsion remained as 2 phases, it was concluded that the continuous phase of the emulsion must be oil since it repels and does not dissolve or disperse into the water; and that thereby the original sample was a water-in-oil emulsion. Conversely, if the emulsion sample easily dissolves or disperses into the water, the original sample was an oil-in-water emulsion.

Chlorhexidine Gluconate (CHG) Compatibility

A 0.5-gram (0.5-g) sample of emulsion (cream formulation) was placed in a vial and shaken with a 50/50 mixture of toluene/ethanol until the cream dissolved. Two drops of HIBICLENS 4% CHG (Zeneca, Wilmington, Del.) were added and the solution allowed to stand for 5 minutes. Five drops of common bleach (5.25% sodium hypochlorite) were added and the solution shaken for 2 minutes. The presence of a brown color indicated that the cream did not inactivate the CHG. If a brown color did not appear, it was concluded that the CHG had been converted to an insoluble salt and was no longer available in solution to be an active antimicrobial agent.

Substantive Barrier Function

Test Overview. The substantive barrier function of an emulsion (cream) composition was determined on human test subjects by measuring the capacitance of treated and untreated skin following soaking in a water bath. As skin is contacted with water and becomes hydrated the capacitance of the skin increases. If the skin is treated with a composition having substantive barrier properties, then, upon exposure to water, the skin will have less hydration and have a lower capacitance as compared to untreated (control) skin. The difference between the capacitance of treated and untreated skin is used to calculate the substantivity (% reduction in capacitance) for the test composition. This test was utilized only for water-in-oil emulsions that did not contain conductive agents with solubility in the oil phase.

Test Procedure. The steps used to conduct the Substantive Barrier Function test procedure are as follows:

1. A test subject's forearm was washed with ivory soap by passing lathered hands up and down the arm five times slowly with light pressure. The soap was rinsed off with water and the arm dried with a paper towel. At least 10 minutes passed before applying the test composition to the cleaned arm.
2. Using a 2.5-cm×3.0-cm template, two rows of four rectangular sites were marked on the dried forearm. With the arm in a horizontal position, approximately 0.3-ml of test composition was applied by latex-free syringe (Becton Dickinson and Co., Franklin Lakes, N.J.) to each of two test sites and the composition rubbed over the entire rectangular site using a size No. 2 latex tissue finger cote (Ansell Protective Products, Coshocton, Ohio) for a period of 10 seconds. A new finger cote was used for each test site. (Three additional test compositions could be applied to the remaining six sites, with two different test sites used for each composition.)
3. After 15 minutes, the forearm was submersed in a water bath (in a container 56 cm by 36 cm with approximately 10 cm of water) that was kept at 29° C.±3° C. and agitated at about 1000 rpm with an overhead stirrer equipped with a propeller blade (with a pitch of approximately 20 degrees for each of the three blades) immersed in the water approximately 5 cm. A Plexiglas guard (0.6 cm thick) having holes of approximately 1.27 cm diameter to allow for water circulation was used to protect the arm from the propeller blade. To both ends of an approximately 25 cm by 10 cm section of Plexiglas was attached another section of Plexiglas that was about 10 cm by 10 cm at approximately 90 degree with screws. About 40 holes were drilled in each of the end pieces of the guard and about 110 holes were drilled in the longest section of the guard. After keeping the arm submersed in the water-bath for about 12 minutes, the arm was removed from the bath and the test sites immediately covered with a water-soaked paper towel on each site to prevent water loss from the sites prior to measuring skin capacitance.
4. The saturated paper towels were sequentially removed from each test site and the surface water was blotted dry with a paper towel. Within 10 seconds from blotting, the skin capacitance of the site was measured with a DPM 9003 Novameter (NOVA Technology Corporation, Gloucester, Mass.). Each measurement was made by placing the probe in the center of the test site and allowing the probe to equilibrate for 5 seconds using the dL 5 setting on the Novameter.
5. A control for each test site was defined as untreated skin within approximately 1 cm of the test site and the capacitance of each control site was measured with the Novameter in the same manner as for the test sites.
6. Substantivity is defined as the percent (%) reduction in capacitance caused by the test composition. [% Reduction=(capacitance of control sites−capacitance of test sites)×100÷capacitance of control sites]. Each capacitance value was the average of two measurements. The greater the percent reduction in capacitance, the greater the substantive barrier function of the test composition. A value of greater than 15% reduction in capacitance is generally considered sufficient as a substantive barrier cream.

Viscosity

The viscosity of a water-in-oil emulsion (lotion or cream formulation) sample was measured using a Brookfield Viscometer, Model LVT, Brookfield Engineering Laboratories, Stoughton, Mass. The viscosity measurements were taken after allowing the sample to equilibrate for 30 hours±6 hours at 20° C.±3° C. A No. 4 spindle was used at a speed of 6 rpm, as indicated on the viscometer, for creams with a viscosity between 5,000 and 100,000 centipoise. A spindle No. 4 was used at a speed of 3 rpm for creams with a viscosity between 100,000 and 200,000 centipoise. The sample was contained in a 118-ml wide-mouth bottle that was at least about 80% full of the emulsion. The measurement was recorded after the spindle had been turning in the sample for approximately 1 minute.

Starting Materials

Polyacrylate Preparation

A typical preparation of the polyacrylates used in the present invention is detailed as follows:

A mixture of SMA (11.7 parts), IOA (9.9 parts), and PEG475 (5.4 parts) [43/37/20, respectively, weight ratio] was dissolved in ethyl acetate (33 parts) that contained VAZO 67 radical initiator (0.081 part). The solution was contained in a flint glass bottle that was closed with a Teflon-lined metal cap and maintained at 65° C. for 50 hours. Monomer conversion (determined by percent solids measured by loss on drying at 105° C.) was essentially complete at 50 hours. An aliquot of the reaction mixture was diluted with THF to a nominal solids concentration of 0.3 weight percent in order to determine inherent viscosity (IV). The polyacrylate (designated as polyacrylate H) had a measured IV of 1.55 dl/g and a calculated hydrophilic-lipophilic balance (HLB) value of 4.0. Solvent exchange was accomplished by adding isopropyl palmitate (IPP) to the ethyl acetate solution and stripping the lower boiling ethyl acetate on a ROTOVAP evaporator to afford a 25 weight percent solution of polyacrylate in IPP.

Similar to the above procedure, a series of polyacrylates were prepared with different weight ratios of SMA, IOA, LMA, and PEG475. The IV and HLB values for the polyacrylates are provided in Table 1. Also, a series of polyacrylates were prepared by a similar procedure, except that various PEO (i.e., PEG) monomers were substituted for PEG475 and used in different SMA/IOA/PEO monomer weight ratios. In the case of Polyacrylates LL through QQ, the polymers were isolated as 25 weight percent solutions in DIPS. The IV and HLB values for these polyacrylates are provided in Table 2.

TABLE 1

| Polyacrylate | Monomer Weight Percent (%) | | | | HLB | IV (dl/g) |
| --- | --- | --- | --- | --- | --- | --- |
| | SMA | IOA | LMA | PEG475 | | |
| A | 51 | 44 | 0 | 5 | 0.8 | 1.35 |
| B | 49 | 41 | 0 | 10 | 1.6 | 1.35 |
| C | 46 | 39 | 0 | 15 | 2.4 | 1.41 |
| D | 80 | 5 | 0 | 15 | 2.4 | 1.50 |
| E | 74 | 10 | 0 | 16 | 2.5 | 1.24 |
| F | 43 | 37 | 0 | 20 | 3.2 | 1.23 |
| G | 43 | 37 | 0 | 20 | 3.2 | 1.28 |
| H | 43 | 37 | 0 | 20 | 3.2 | 1.55 |
| I | 51 | 29 | 0 | 20 | 3.2 | 1.39 |
| J | 40 | 40 | 0 | 20 | 3.2 | 1.23 |
| K | 25 | 53 | 0 | 22 | 3.5 | 1.17 |
| L | 13 | 64 | 0 | 23 | 3.6 | 1.42 |
| M | 40 | 35 | 0 | 25 | 4.0 | 1.19 |
| N | 30 | 30 | 0 | 40 | 6.3 | 1.26 |
| AA | 43 | 37 | 0 | 20 | 3.2 | 1.23 |
| BB | 36.25 | 36.25 | 0 | 27.5 | 4.3 | 1.29 |
| CC | 35 | 35 | 0 | 30 | 4.7 | 1.46 |
| DD | 33.75 | 33.75 | 0 | 32.5 | 5.1 | 1.35 |
| EE | 32.5 | 35.5 | 0 | 35 | 5.5 | 1.19 |
| FF | 31.25 | 31.25 | 0 | 37.5 | 5.9 | 1.2 |
| GG | 0 | 80 | 0 | 20 | 3.2 | 1.56 |

TABLE 1-continued

| Polyacrylate | Monomer Weight Percent (%) | | | | HLB | IV (dl/g) |
| --- | --- | --- | --- | --- | --- | --- |
| | SMA | IOA | LMA | PEG475 | | |
| HH | 80 | 0 | 0 | 20 | 3.2 | 1.08 |
| II | 36.25 | 0 | 36.25 | 27.5 | 4.3 | 1.04 |
| JJ | 0 | 36.25 | 36.25 | 27.5 | 4.3 | 1.84 |
| KK | 0 | 0 | 72.5 | 27.5 | 4.3 | 1.04 |

TABLE 2

| Polyacrylate | Monomer Weight Percent (%) | | | HLB | IV (dl/g) |
| --- | --- | --- | --- | --- | --- |
| | SMA | IOA | PEO Monomer - % | | |
| O | 40 | 35 | EEEA - 25 | 2.3 | 1.43 |
| P | 48 | 42 | PEG1100 - 10 | 1.8 | 1.38 |
| Q | 44 | 37 | PEG1100 - 19 | 3.5 | 1.71 |
| R | 40 | 35 | PEG1100 - 25 | 4.6 | 1.22 |
| S | 48 | 42 | PEG300 - 10 | 1.3 | 1.57 |
| T | 45 | 40 | PEG300 - 15 | 2.0 | 1.45 |
| U | 43 | 39 | PEG300 - 18 | 2.4 | 1.08 |
| V | 40 | 35 | PEG300 - 25 | 3.3 | 1.57 |
| LL | 51 | 44 | M90G - 5 | 0.8 | 1.04 |
| MM | 49 | 41 | M90G - 10 | 1.5 | 1.13 |
| NN | 46 | 39 | M90G - 15 | 2.3 | 1.30 |
| OO | 43 | 37 | M90G - 20 | 3.1 | 1.40 |
| PP | 51 | 29 | M90G - 20 | 3.1 | 1.35 |
| QQ | 40 | 40 | M90G - 20 | 3.1 | 1.49 |

Examples 1-29

Water-in-Oil Emulsion (Cream) Preparations

Emulsion Preparation A (Examples 1-15)

A typical preparation of a water-in-oil emulsion (cream formulation) of the present invention is detailed as follows (Preparation A):

Oil Phase ingredients and Water Phase ingredients are listed in Table 3 and Table 4. The Oil Phase ingredients were placed in a stainless steel beaker and heated on a steam bath at 94° C. with minimal stirring for about 30 minutes at which point the solution was homogenous. The Water Phase ingredients were placed in another stainless steel beaker and heated to 94° C. on a hot plate. With moderate stirring, the Water Phase was added to the Oil Phase over about 15 minutes. With continued stirring, the temperature was maintained at above 93° C. for an additional 15 minutes after which time the resulting solution was allowed to slowly cool. When the solution temperature reached 71° C., dimethicone, 1000 CST skin barrier/protectant (1.3 parts, Dow Corning, Midland, Mich.) was added; and, with continued stirring, when the temperature reached 49° C., GERMABEN II preservative (0.8 part, ISP-Sutton Labs, Catham, N.J.) and polyethylene thickener (10.32 parts, Allied Signal, Morristown, N.J.) were added. At a temperature of 35-45° C., the particle size of the resulting mixture was reduced by stirring at 1300-1700 with a high shear dispersing impeller for approximately 10 minutes.

TABLE 3

| Oil Phase | | | |
| --- | --- | --- | --- |
| Ingredient | Function | Parts | Source |
| Polyacrylate (25% in IPP) | Substantivity | 7.18 | See Polyacrylate Preparation above |

TABLE 3-continued

| Oil Phase | | | |
| --- | --- | --- | --- |
| Ingredient | Function | Parts | Source |
| ESTANSAN GT-8-60 (Glyceryl tricaprylate/caprate) | Emollient oil | 2.7 | Unichema Chicago, IL |
| Paraffin | Emollient oil | 1.2 | Union Oil of CA Los Angeles, CA |
| ARLACEL P135 (PEG(30) Polyhydroxy-stearate, MW approximately 5000) | Auxiliary emulsifier (Surfactant) | 2.37 | ICI Wilmington, DE |
| Coconut Oil | Emollient oil | 6.7 | Universal Edible Oils Chicago, IL |
| Dicapryl Adipate | Emollient oil | 10.1 | Union Camp Corp. Wayne, NJ |
| PPG(15) Stearyl Ether | Auxiliary emulsifier and Emollient oil | 5.53 | Ruger Chemical Co. Irvington, NJ |

TABLE 4

| Water Phase | | | |
| --- | --- | --- | --- |
| Ingredient | Function | Parts | Source |
| Water | Solvent | 44.91 | |
| Magnesium Sulfate Heptahydrate | Stabilizer | 1.5 | Mallinckrodt Inc. Paris, KY |
| Dipropylene Glycol | Humectant | 5.39 | ChemCentral Lakeville, MN |

Following this Preparation A, stable water-in-oil emulsions (cream formulations) were prepared using polyacrylates C through M (Examples 1-11, respectively), P through R (Examples 12-14, respectively), and V (Example 15); whereas, polyacrylate N produced an emulsion that failed the Emulsion Stability Test; and no emulsions were formed under these conditions with polyacrylates A, B, O, and S through U. It appears that the formation of stable water-in-oil emulsions is dependent on the HLB of the polymer used in the formulation. The range of HLBs that yield stable water-in-oil emulsions varies with each polymer class.

Emulsion Preparation B (Examples 16-26)

Emulsion Preparation B was carried out in the same manner as Preparation A, except that the water phase (See Table 4) contained only water (46.41 parts) and dipropylene glycol (5.39 parts). Therefore, the water phase of Preparation B did not contain any magnesium sulfate heptahydrate.

Following this Preparation B, stable water-in-oil emulsions (cream formulations) were prepared using polyacrylates M (Example 16), AA through EE (Examples 17-21, respectively), and GG-KK (Examples 22-26, respectively); whereas, polyacrylates D, N, and FF produced emulsions that failed the Emulsion Stability Test.

Emulsion Preparation C (Examples 27-28)

Emulsion Preparation C was carried out in the same manner as Preparation A, except that the oil phase contained 0, 1.0, 2.0, or 4.0 parts of the polyacrylate G (25% in IPP) and additional water was added to make up for the difference.

Following this Preparation C, stable water-in-oil emulsions (cream formulations) were prepared using either 4.0 parts (Example 27) or 2.0 parts (Example 28) polyacrylate in the oil phase; a water-in-oil emulsion (cream formulation) was prepared using 1.0 part polyacrylate, however, the emulsion failed the Emulsion Stability Test; and no emulsion formed when using 0 part polyacrylate in the oil phase.

Emulsion Preparation D (Example 29)

Emulsion Preparation D was carried out in the same manner as Preparation B, except that the oil phase contained 3.0 or 5.0 parts of the polyacrylate BB (25% in IPP) and additional water was added to make up for the difference.

Following this Preparation D, a stable water-in-oil emulsion (cream formulation) was prepared using 5.0 parts (Example 29) polyacrylate in the oil; however, the water-in-oil emulsion (cream formulation) prepared using 3.0 parts polyacrylate failed the Emulsion Stability Test.

Example 30

Water-in-Oil Emulsion (Cosmetic Formulation) Preparation

Emulsion Preparation E (Example 30)

A typical preparation of a water-in-oil emulsion (cosmetic formulation) of the present invention is detailed as follows (Preparation E):

Oil Phase ingredients and Water Phase ingredients are listed in Table 5 and Table 6. The Polyacrylate F component was added in the form of an isodecane solution to the other Oil Phase ingredients and the resulting mixture heated to 80-85° C. In a separate vessel, the Water Phase ingredients were mixed and heated to 80-85° C. The heated Oil Phase was mixed with a homogenizer and the heated Water Phase slowly added. The resulting mixture was homogenized at high speed for 10 minutes and then allowed to slowly cool to room temperature with gentle mixing.

TABLE 5

Oil Phase

| Ingredient | Parts | Source |
| --- | --- | --- |
| Polyacrylate F in Isododecane (Parts based on 100% solids) | 1.3 | See Polyacrylate Preparation above |
| Vitamin E Acetate | 0.2 | Sigma-Aldrich Chemical, St. Louis, MO |
| BRIJ 30 (laureth-4) | 0.6 | ICI, Wilmington, DE |
| Stearic Acid | 2.2 | J. T. Baker Inc., Phillipsburg, NJ |
| Isododecane | 15.7 | PermethylSpec.LLC, Melmay, NJ |
| Isooctane | 14.8 | PermethylSpec.LLC, Melmay, NJ |

TABLE 6

Water Phase

| Ingredient | Parts | Source |
| --- | --- | --- |
| Water | 44.9 | DI Water |
| Dipropylene Glycol | 3.0 | Lyondell Chemical, Houston, TX |
| Polysiloxy Linoleyl Pyrrolidone Phospholipid | 1.7 | Mona Industries, Paterson, NJ |
| Triethanol Amine | 0.7 | Dow Chemical, Midland, MI |
| Methylparaben | 0.3 | Costec Inc., Palatine, IL |
| Propylparaben | 0.1 | Costec Inc., Palatine, IL |
| Sodium Magnesium Silicate | 0.9 | Southern Clay, Gonzales, TX |
| Magnesium Aluminum Silicate | 2.1 | R. T. Vanderbilt, Norwalk, CT |
| Yellow Iron Oxide | 0.9 | Cardre, South Plainfield, NJ |
| Titanium Dioxide | 7.0 | Cardre, South Plainfield, NJ |
| Talc | 3.3 | Luzenac America, Englewood, CO |
| Red Iron Oxide | 0.7 | Cardre, South Plainfield, NJ |
| Black Iron Oxide | 0.1 | Cardre, South Plainfield, NJ |

The stable water-in-oil emulsion produced by Procedure E (Example 30) was evaluated as a transfer resistant color cosmetic formulation as described under the Evaluations and Results section of these Examples and is representative of the various types of personal care or cosmetic products that can be formulated from the stable water-in-oil emulsions of the present invention. In contrast to the very tacky nature of the Polyacrylate F ingredient, the Example 30 emulsion (lotion) was essentially non-tacky to the touch.

Examples 31-39

Water-in-Oil Emulsion (Tissue Disinfectant) Preparations

Emulsion Preparation F (Examples 31-36)

A typical preparation of a water-in-oil emulsion (tissue disinfectant, i.e., antiseptic) of the present invention is detailed as follows (Preparation F):

Oil Phase ingredients and Water Phase ingredients are listed in Table 7 and Table 8. The Oil Phase ingredients were combined and heated at 100° C. for 2 hours. In a separate vessel, the Water Phase ingredients were combined and heated at 100° C. for 15 minutes. The heated Water Phase was added to the heated Oil Phase over about 1 minute with agitation using a Silverson homogenizer (2.54-cm diameter high-shear head) on high speed followed by continuous mixing for another 1 minute at high speed. The resulting emulsion was placed in a steam jacket and mixed with an overhead air motor and T-shaped impeller at steam temperature (about 80° C.) for 15 minutes with vigorous overhead stirring and then slowly cooled to 40° C. The emulsion was then removed from the mixing apparatus and allowed to cool to room temperature.

Following this Preparation F, stable water-in-oil emulsions were prepared using polyacrylates OO, PP, and QQ (Examples 31-33, respectively, that were stable (i.e., no separation of the components) through 3 freeze-thaw cycles of the Emulsion Stability Test); whereas the emulsion prepared from polyacrylate NN (Example 34) was only stable only through 1 cycle of the test; and the emulsions prepared from polyacrylates LL and MM (Examples 35 and 36, respectively) were not stable (emulsions separated on standing overnight). Examples 31-33 were evaluated as skin preparations as described in the Evaluations and Results section of these Examples.

TABLE 7

Oil Phase

| Ingredient | Parts | Source |
| --- | --- | --- |
| Polyacrylate (25 wt-% in DIPS) | 12 | See Polyacrylate Preparation above |
| Ethylene/Acrylic Acid (AC540) | 2.5 | Allied Signal, Morristown, NJ |
| Dioctyl Cyclohexane (CETIOL S) | 5 | Henkel, Hoboken, NJ |
| DIPS | 20 | Alzo |
| ARLAMOL E (PPG (15) Stearyl Ether) | 6 | ICI, Wilmington, DE (now Uniqema) |

TABLE 8

Water Phase

| Ingredient | Parts | Source |
| --- | --- | --- |
| Water | 49.5 | DI water |
| $MgSO_4 \cdot 7H_2O$ | 0.5 | Sigma-Aldrich Chemical |
| PVP/Iodine 30% Solution (pH adjusted to 4.3 with 5N NaOH) | 10 | BASF, Wyandotte, MI |

Emulsion Preparation G (Examples 37-39)

A typical preparation of a water-in-oil emulsion (tissue disinfectant) of the present invention is detailed as follows (Preparation G): Oil Phase ingredients and Water Phase ingredients are listed in Table 9 and Table 10. The Oil Phase ingredients were combined and heated at 100° C. for 2 hours. In a separate vessel, the Water Phase ingredients were combined and heated at 100° C. for 15 minutes. The heated Water Phase was added (by hand for Polyacrylate QQ Water Phase and with a peristaltic pump for Polyacrylate OO and PP Water Phases) to the heated Oil Phase over about 5 minutes. During the addition the contents were mixed with a Silverson homogenizer (2.54-cm diameter high-shear head) on three-quarters speed followed by continuous mixing for another 2 minutes at full speed. The Oil Phase was heated on a hot plate to maintain temperature throughout the addition. After about three-quarters of the Water Phase had been added, a noticeable thickening of the emulsion was observed. The resulting emulsion was mixed with an overhead mixer at high speed while the emulsion slowly cooled to 40° C. The emulsion was then removed from the mixing apparatus and allowed to cool to room temperature.

Following this Preparation G, stable water-in-oil emulsions were prepared using polyacrylates OO, PP, and QQ (Examples 37-39, respectively, that were stable (i.e., no separation of the components) through 3 freeze-thaw cycles of the Emulsion Stability Test). Examples 37-39 were evaluated as skin preparations as described in the Evaluations and Results section of these Examples.

TABLE 9

| Oil Phase | | |
|---|---|---|
| Ingredient | Parts | Source |
| Polyacrylate (25 wt-% in DIPS) | 8 | See Polyacrylate Preparation above |
| Ethylene/Acrylic Acid (AC540) | 2.5 | Allied Signal |
| Dioctyl Cyclohexane (CETIOLS) | 5 | Henkel |
| DIPS | 20 | Alzo |
| PPG (15) Stearyl Ether | 6 | ICI |

TABLE 10

| Water Phase | | |
|---|---|---|
| Ingredient | Parts | Source |
| Water | 18.8 | DI water |
| $MgSO_4 \cdot 7H_2O$ | 0.5 | Sigma-Aldrich Chemical |
| Citric Acid | 0.2 | Sigma-Aldrich Chemical |
| Dimethyl Isosorbide (DMI) | 5.0 | Uniqema, Wilmington, DE |
| PVP/Iodine 30% Solution (pH adjusted to 4.3 with 5N NaOH) | 33 | BASF |

Examples 40-42

Water-in-Oil Emulsion Preparations (with ARLACEL P135)

Emulsion Preparation H (Example 40—COMPARATIVE)

Emulsion Preparation H was carried out in the same manner as Preparation A, except for the following: the Oil Phase was as shown in Table 3, except that it contained no polyacrylate, 2 parts of a polymeric emulsifier (commercially available under the trade designation ARLACEL P135 from ICI), 2.7 parts of squalane in place of glycerol tricaprylate/caprate, and an added 5.18 parts of IPP; the Water Phase (See Table 4) contained only 46.41 parts of water and 5.39 parts of dipropylene glycol (no magnesium sulfate heptahydrate). The resulting stable water-in-oil emulsion (Example 40) was evaluated for substantivity and compared to selected polyacrylate-containing emulsions of the present invention. (See Table 15)

Emulsion Preparation I (Example 41)

A water-in-oil emulsion (tissuedisinfectant) of the present invention was prepared using the Oil Phase and Water Phase ingredients that are listed in Tables 11 and 12. The Preparation I was then carried out in the same manner as Preparation G with the addition of the Water Phase to the Oil Phase by hand. The resulting water-in-oil emulsion (Example 41) was found to be basically stable with only a trace (about 0.01 ml) of separation observed after 3 freeze-thaw cycles of the Emulsion Stability Test.

TABLE 11

| Oil Phase | |
|---|---|
| Ingredient | Parts |
| ARLACEL P135 (PEG(3)) Polyhydroxy-stearate, MW approximately 5000) | 6 |
| DIPS | 16.5 |
| ARLAMOL E (PPG (15) Stearyl Ether) | 7.5 |

TABLE 12

| Water Phase | |
|---|---|
| Ingredient | Parts |
| Water | 59.8 |
| Citric Acid | 0.2 |
| PVP/Iodine 30% Solution (pH adjusted to 3.3 with 5N NaOH) | 10 |

Emulsion Preparation J (Example 42)

A water-in-oil emulsion (tissue disinfectant) of the present invention was prepared using the Oil Phase and Water Phase ingredients that are listed in Tables 13 and 14. The Preparation J was then carried out in the same manner as Preparation G, except with the addition of the Water Phase to the Oil Phase by hand over about 2 minutes and with the Silverson homogenizer on half-speed during the addition. The resulting water-in-oil emulsion (Example 42) was found to be stable in the Emulsion Stability Test and was evaluated as a skin preparation as described in the Evaluations and Results section of these Examples.

TABLE 13

| Oil Phase | |
|---|---|
| Ingredient | Parts |
| ARLACEL P135 (PEG(3)) Polyhydroxy-stearate, MW approximately 5000) | 4.005 |
| DIPS | 16.02 |
| ARLAMOL E (PPG (15) Stearyl Ether) | 6.675 |

TABLE 14

| Water Phase | |
|---|---|
| Ingredient | Parts |
| MgSO$_4$•7H$_2$O | 2.7 |
| Dimethyl Isosorbide (DMI) | 4 |
| Premix of PVP/Iodine (10% Aqueous Solution) containing 0.5% MgSO$_4$•7H$_2$O and 2% citric acid (adjusted to pH of 3.3 with 5N NaOH) | 34.16 |

Evaluations and Results

Emulsion Test Results

All of the stable emulsions of the present invention not containing povidone-iodine were evaluated with an electrical emulsion tester as described in the Emulsion Conductivity Test method described herein and found to be water-in-oil emulsions. Those stable emulsions that did contain povidone-iodine were evaluated in the Emulsion Dilution Test method described herein and found to be water-in-oil emulsions.

Chlorhexidine Gluconate (CHG) Compatibility Results

Certain of the stable water-in-oil emulsions of the present invention were evaluated for Chlorhexidine Gluconate compatibility according to the CHG compatibility test method described herein. Stable water-in-oil emulsions prepared according to Water-in-Oil Emulsion Preparation A were generally found to be not compatible with (i.e., to inactivate) CHG. This result is attributed to the presence of the magnesium sulfate heptahydrate ingredient in the emulsion. Stable water-in-oil emulsions prepared according to Water-in-Oil Emulsion Preparation B (that excluded the magnesium sulfate heptahydrate ingredient) were generally found to be compatible with CHG.

Additionally, stable water-in-oil emulsions prepared containing acrylic acid instead of poly(ethyleneglycol) (meth)acrylate monomer in the polyacrylate component (prepared as in Preparation B), were found to inactivate CHG when evaluated by the CHG compatibility test method.

Substantive Barrier Function Results

Certain of the stable water-in-oil emulsions of the present invention were evaluated for a substantive barrier function according to the method described herein and the results are provided in Table 15. These results show that the polyacrylate-based water-in-oil emulsions (Examples 2-4, 9-12, 14-29) had good substantivity (greater than 15% reduction of skin capacitance) and would be expected to be effective as substantive barrier creams. In contrast, Example 40 that contained the polymeric emulsifier available under the trade designation ARLACEL P135 from ICI, in place of the polyacrylate showed poor substantivity (9% reduction of skin capacitance as shown in Table 15).

TABLE 15

| Example | Polyacrylate | Emulsion Preparation | Cream Viscosity (Centipoise) | Substantivity (% Reduction of Skin Capacitance) |
|---|---|---|---|---|
| 2 | D | A | NM* | 57 |
| 3 | E | A | NM | 53 |
| 4 | F | A | NM | 55 |
| 9 | K | A | NM | 60 |
| 10 | L | A | NM | 65 |
| 11 | M | A | NM | 62 |
| 12 | P | A | NM | 49 |
| 14 | R | A | NM | 49 |
| 15 | V | A | NM | 53 |
| 16 | M | B | 124,000 | 49 |
| 17 | AA | B | 170,000 | 38 |
| 18 | BB | B | 68,000 | 40 |
| 19 | CC | B | 68,000 | 51 |
| 20 | DD | B | 70,000 | 57 |
| 21 | EE | B | 65,000 | 54 |
| 22 | GG | B | 100,000 | 51 |
| 23 | HH | B | 154,000 | 53 |
| 24 | II | B | 68,000 | 39 |
| 25 | JJ | B | 69,000 | 48 |
| 26 | KK | B | 64,000 | 54 |
| 27 | G | C | NM | 48 |
| 28 | G | C | NM | 59 |
| 29 | BB | D | NM | NM |
| 40 COMP. | None | A | NM | 9 |

*NM—Not Measured

Cosmetic Material Transfer Resistance Results

Example 30 is representative of the various types of personal or cosmetic materials that can be made with the water-in-oil emulsions of the present invention. This is best seen by making a control formula in which the polymer solids are replaced by cetyl alcohol (available from Croda, Parsippany, N.J.) followed by a rub off test. The rub off test was done by applying a small amount of test formula to the skin and allowing it to dry, followed by lightly rubbing the test area with a white paper towel 5 times. The water-in-oil emulsion of Example 30 showed dramatic reduction in level of color pigment transferred to the towel when compared to the cetyl alcohol control.

Evaluation of Tissue Disinfectants

Emulsion Examples 31-33 and Examples 37-39 were applied to skin as a thin film with a polyurethane sponge and found to spread very easily and uniformly. After time periods of both 1 and 5 minutes, an incise drape (commercially available under the trade designation IOBAN II from 3M Co.) was applied to the emulsion-coated skin and found to adhere very well. Similarly, Example 42 was applied to skin and the incise drape found to have low adhesion to the coated skin when applied for 1 minute, but to have good adhesion when applied for 5 minutes.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of disinfecting skin or mucosal tissue, the method comprising applying an antimicrobial composition to the skin or mucosal tissue, wherein the antimicrobial composition comprises an antimicrobial agent, and a water-in-oil emulsion comprising a vinyl polymer comprising the reaction product of at least two monomers comprising: (i) polyethylene oxide methacrylate and (ii) at least about 60 wt-%, based on the total weight of the polymerizable composition, of one or more alkyl(meth)acrylic monomers wherein the alkyl group has at least 4 carbon atoms on average, an oil phase and an aqueous phase.

2. The method of claim 1 wherein the composition is substantive.

3. The method of claim 1 wherein the composition allows adhesion of pressure sensitive adhesive products.

4. The method of claim 1 wherein the vinyl polymer comprises ethylene oxide-containing side chains and alkyl-Y-containing side chains, wherein Y is O or NR, wherein R is H or $CH_3$, and the alkyl group has at least 4 carbon atoms on average in a cyclic, branched-, or straight-chain configuration and optionally includes one or more heteroatoms.

5. The method of claim 1 wherein the composition further comprises a polyetherpolyester polymer.

6. The method of claim 1 wherein the composition further comprises a buffer.

7. The method of claim 1 wherein the composition further comprises an auxiliary emulsifier.

8. The method of claim 1 wherein the antimicrobial agent is selected from the group consisting of iodine, an iodophor, a chlorhexidine salt, parachlorometaxylenol, triclosan, hexachlorophene, a fatty acid monoester of glycerin or propylene glycol, a surfactant or polymer that includes a $C_{12}$-$C_{22}$ hydrophobe and a quaternary ammonium group, a polyquaternary amine, a quaternary silane, hydrogen peroxide, silver, a silver salt, and combinations thereof.

9. A water-in-oil emulsion comprising:
an antimicrobial agent; and
a vinyl polymer comprising the reaction product of at least two monomers comprising: (i) polyethylene oxide methacrylate and (ii) one or more alkyl (meth)acrylic monomers wherein the alkyl group has at least 4 carbon atoms on average;
an oil phase; and
a water phase.

10. The water-in-oil emulsion of claim 9, wherein the one or more alkyl(meth)acrylic monomers are present in an amount of at least about 60 wt-%, based on the total weight of the polymerizable composition.

11. A water-in-oil emulsion comprising:
a vinyl polymer comprising the reaction product of at least two monomers comprising: (i) polyethylene oxide methacrylate and (ii) at least about 60 wt-%, based on the total weight of the polymerizable composition, of one or more alkyl (meth)acrylic monomers wherein the alkyl group has at least 4 carbon atoms on average;
an oil phase; and
a water phase.

12. The water-in-oil emulsion of claim 11, wherein the one or more alkyl(meth)acrylic monomers are selected from the group consisting of isooctyl acrylate, 2-ethylhexyl acrylate, and combinations thereof.

13. A moisturizing composition comprising a water-in-oil emulsion comprising:
a vinyl polymer comprising the reaction product of at least two monomers comprising: (i) polyethylene oxide methacrylate and (ii) at least about 60 wt-%, based on the total weight of the polymerizable composition, of one or more alkyl (meth)acrylic monomers wherein the alkyl group has at least 4 carbon atoms on average;
an oil phase; and
a water phase;
wherein the moisturizing composition has a substantivity of greater than 15% as measured by the Substantive Barrier Function Test Procedure.

14. The moisturizing composition of claim 13, wherein the one or more alkyl(meth)acrylic monomers are selected from the group consisting of isooctyl acrylate, 2-ethylhexyl acrylate, and combinations thereof.

15. A tissue antiseptic composition comprising an antimicrobial agent and a water-in-oil emulsion comprising:
a vinyl polymer comprising the reaction product of at least two monomers comprising: (i) polyethylene oxide methacrylate and (ii) at least about 60 wt-%, based on the total weight of the polymerizable composition, of one or more alkyl (meth)acrylic monomers wherein the alkyl group has at least 4 carbon atoms on average;
an oil phase; and
a water phase.

16. The tissue antiseptic composition of claim 15, wherein the one or more alkyl(meth)acrylic monomers are selected from the group consisting of isooctyl acrylate, 2-ethylhexyl acrylate, and combinations thereof.

17. A personal care composition comprising a water-in-oil emulsion comprising:
a vinyl polymer comprising the reaction product of at least two monomers comprising: (i) polyethylene oxide methacrylate and (ii) at least about 60 wt-%, based on the total weight of the polymerizable composition, of one or more alkyl (meth)acrylic monomers wherein the alkyl group has at least 4 carbon atoms on average;
an oil phase;
a water phase; and
at least one additive selected from the group consisting of conditioners, sunscreen agents, insect repellents, vitamins, herbal extracts, antiperspirant agents, deodorant agents, skin bleaching agents, skin coloring agents, hair bleaching agents, hair coloring agents, sunless tanning agents, depilating agents, antidandruff agents, antiacne agents, astringents, tensors, skin toning agents, corn removers, callus removers, wart removers, glitter, pigments, dyes, bleaches, perfumes, and fragrances.

18. The personal care composition of claim 17, wherein the one or more alkyl(meth)acrylic monomers are selected from the group consisting of isooctyl acrylate, 2-ethylhexyl acrylate, and combinations thereof.

19. A transdermal drug delivery composition comprising a pharmaceutical agent and a water-in-oil emulsion comprising:
a vinyl polymer comprising the reaction product of at least two monomers comprising: (i) polyethylene oxide methacrylate and (ii) at least about 60 wt-%, based on the total weight of the polymerizable composition, of one or more alkyl (meth)acrylic monomers wherein the alkyl group has at least 4 carbon atoms on average;
an oil phase; and
a water phase.

20. The transdermal drug delivery composition of claim 19, wherein the one or more alkyl(meth)acrylic monomers are selected from the group consisting of isooctyl acrylate, 2-ethylhexyl acrylate, and combinations thereof.

21. The water-in-oil emulsion of claim 11, further comprising an auxiliary emulsifier.

22. The water-in-oil emulsion of claim 11, wherein the water phase comprises a humectant.

23. The water-in-oil emulsion of claim 11, further comprising a silicone oil dimethicone in the oil phase.

* * * * *

UNITED STATES PATENT AND TRADEMARK OFFICE
CERTIFICATE OF CORRECTION

| | | |
|---|---|---|
| PATENT NO. | : 8,026,327 B2 | Page 1 of 1 |
| APPLICATION NO. | : 11/256135 | |
| DATED | : September 27, 2011 | |
| INVENTOR(S) | : Deral T. Mosbey | |

It is certified that error appears in the above-identified patent and that said Letters Patent is hereby corrected as shown below:

Page 1, Column 1, Item 62 (Related U.S. Application Data)
Line 1, Delete "Division" and insert -- Continuation --, therefor.

Column 1
Line 10, After "7,030,203" insert -- . --.

Column 4
Line 18, Delete "pressure" and insert -- Pressure --, therefor.

Column 10
Line 31, Delete "diiospropyl" and insert -- diisopropyl --, therefor.

Column 12
Line 51, Delete "precatherization" and insert -- precatheterization --, therefor.

Column 14
Line 28, Delete "STER1" and insert -- STERI --, therefor.

Column 15
Line 6, Delete "diiospropylsebacate, isopropylplamitate," and insert
      -- diisopropylsebacate, isopropylpalmitate, --, therefor.
Line 7, Delete "diiosnonanoate," and insert -- diisononanoate, --, therefor.

Column 17
Line 30, Delete "Sayerville," and insert -- Sayreville, --, therefor.

Signed and Sealed this
Twelfth Day of June, 2012

David J. Kappos
*Director of the United States Patent and Trademark Office*